(12) United States Patent
Gao et al.

(10) Patent No.: US 11,052,176 B2
(45) Date of Patent: Jul. 6, 2021

(54) GRADIENT COATINGS OF BIOPEPTIDES THAT PROMOTE ENDOTHELIAL CELLS SELECTIVE ADHESION AND DIRECTIONAL MIGRATION AND METHODS OF USING THE SAME

(71) Applicant: Zhejiang University, Hangzhou (CN)

(72) Inventors: Changyou Gao, Hangzhou (CN); Shan Yu, Hangzhou, WA (US); Zhengwei Mao, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 15/728,523

(22) Filed: Oct. 10, 2017

(65) Prior Publication Data

US 2020/0139010 A1    May 7, 2020

(51) Int. Cl.
| | | |
|---|---|---|
| *A61F 2/07* | (2013.01) |
| *A61K 9/70* | (2006.01) |
| *A61L 27/22* | (2006.01) |
| *A61L 27/34* | (2006.01) |
| *A61L 27/54* | (2006.01) |
| *A61L 27/36* | (2006.01) |

(Continued)

(52) U.S. Cl.
CPC .............. *A61L 27/362* (2013.01); *A61K 9/70* (2013.01); *A61K 9/7007* (2013.01); *A61L 27/227* (2013.01); *A61L 27/34* (2013.01); *A61L 27/3625* (2013.01); *A61L 27/3808* (2013.01); *A61L 27/507* (2013.01); *A61L 27/54* (2013.01); *A61L 27/58* (2013.01); *C12N 5/0691* (2013.01); *A61F 2210/0076* (2013.01); *A61F 2310/00976* (2013.01); *A61L 2300/252* (2013.01); *A61L 2300/604* (2013.01); *A61L 2300/61* (2013.01); *A61L 2300/64* (2013.01); *A61L 2400/18* (2013.01); *A61L 2430/40* (2013.01)

(58) Field of Classification Search
CPC ... A61F 2210/0076; A61F 2310/00976; A61K 9/7007; A61L 27/227; A61L 27/34; A61L 27/3808; A61L 27/507; A61L 27/54; A61L 2300/608; A61L 2300/61; A61L 2400/18
See application file for complete search history.

(56) References Cited

PUBLICATIONS

Taub et al., The Journal of Experimental Medicine, vol. 177, Jun. 1993, 1809-181. (Year: 1993).*

(Continued)

*Primary Examiner* — Jeffrey E. Russel

(57) ABSTRACT

A two-layer gradient coating article is provided that is operable to cause selective adhesion and directional migration of endothelial cells. The first layer includes cell-resisting polymers that repels cells, the second layer includes one layer of peptides that has affinity to and binds specifically to endothelial cells. Furthermore, the peptides are distributed in a gradient, in which attached ECs migrate towards the direction of increased concentration, thus enriching the ECs to a desired locus. The combination of a cell-repelling layer and a graded affinity peptide produces a unique result of selective adhesion, directional migration, thus local enrichment of endothelial cells. A method for using such gradient coating article and its potential use in treating cardiovascular diseases are also provided. The invention provides an inexpensive, stable and effective means for attracting ECs to desirable locations.

16 Claims, 27 Drawing Sheets
(4 of 27 Drawing Sheet(s) Filed in Color)
Specification includes a Sequence Listing.

(51) Int. Cl.
*C12N 5/071* (2010.01)
*A61L 27/38* (2006.01)
*A61L 27/58* (2006.01)
*A61L 27/50* (2006.01)

(56) References Cited

PUBLICATIONS

Yu et al., ACS Appl. Mater. Interfaces, 2016, 8, 29280-29288. (Year: 2016).*
And evidenced by Mather et al., Prog. Polym. Sci., 2006, 31,487-531. (Year: 2006).*
Kolka et al., Rev Endocr Metab Disord., Mar. 2013; 14(1): 13-19. (Year: 2013).*
N. Ayres. Polymer brushes: Applications in biomaterials and nanotechnology. Polymer Chemistry. 2010, vol. 1, pp. 769-777. (Year: 2010).*
Tsai et al. Vapor-Based Multicomponent Coatings for Antifouling and Biofunctional Synergic Modifications. Advanced Functional Materials. 2014, vol. 24, pp. 2281-2287. (Year: 2014).*

\* cited by examiner

GRADIENT COATINGS OF BIOPEPTIDES THAT PROMOTE ENDOTHELIAL CELLS SELECTIVE ADHESION AND DIRECTIONAL MIGRATION AND METHODS OF USING THE SAME

FIELD

This application relates in general to biopolymers and, in particular, to compositions in the form of coatings that promotes selective adhesion and directional migrations of endothelial cells.

BACKGROUND OF THE INVENTION

Endothelium, composed of endothelial cells (ECs), is essential in preventing intimal thickening, maintaining blood fluidity, and improving thromboresistance in the applications of many cardiovascular implants such as stents, vascular grafts, and heart valves. [de Mel A, Jell G, Stevens M M, Seifalian A M. Biofunctionalization of biomaterials for accelerated in situ endothelialization: A review, *Biomacromolecules* 2008; 9: 2971-2979.] During endothelium healing or regeneration process, i.e. creating a lining of living ECs, correct cell adhesion and following directional migration of endothelial cells are key events. Cell adhesion is a pre-required step for many physiological processes such as migration, proliferation and differentiation, by which cells interact and attach to a surface, substrate or another cell, mediated by interactions between molecules of the cell surface [Gumbiner, B. M. (1996). "Cell Adhesion: The Molecular Basis of Tissue Architecture and Morphogenesis". Cell. 84 (3): 345-357.] Cell migration is a central process in the development and maintenance of multicellular organisms. Tissue formation, wound healing and immune responses all require the orchestrated movement of cells in particular directions to specific locations. Cells often migrate in response to specific external signals, including chemical signals and mechanical signals [Mak, M.; Spill, F.; Roger, K.; Zaman, M. "Single-Cell Migration in Complex Microenvironments: Mechanics and Signaling Dynamics". Journal of biomechanical engineering. 138(2):37-44]

Undesired cell adhesion and migration will cause diseases or improper regeneration of tissues such as atherosclerosis, a chronic inflammatory disease of arterial wall [Almodovar, J.; Crouzier, T.; Selimovic, S.; Boudou, T.; Khademhosseini, A.; Picart, C. Gradients of Physical and Biochemical Cues on Polyelectrolyte Multilayer Films Generated via Microfluidics. Lab Chip 2013, 13, 1562-1570.] During atherosclerosis, endothelium is damaged, and subsequent adhesion and migration of other cells such as vascular smooth muscle cells (SMCs) and fibroblasts, which naturally move much faster than ECs to the impaired vessels, is stimulated by various inflammatory factors, leading to further damage of the vasculature. Therefore, a faster ECs migration and adhesion to the damaged endothelial location might reduce or prevent the sequence of events that leads to the occurrence of atherosclerotic lesions. In-stent restenosis (ISR), a particular refractory form of neointimal hyperplasia [Amatruda, C.; Casas, C.; Keller, B.; Tahir, H.; Dubini, G.; Hoekstra, A. From Histology and Imaging Data to Models for In-stent Restenosis. International journal of artificial organs 2014, 37, 786-800.] is another example wherein selective adhesion and directional migration of ECs may have profound impact on cardiovascular disease onset and progression. Stent implantation has become a main method to treat coronary artery diseases. However, the implantation may induce a series of pathological processes such as thrombosis and abnormal release of cytokines. These pathological events subsequently trigger the migration and proliferation of SMCs and fibroblasts, and thereby induce ISR [Galis, Z.; Johnson, C.; Godin, D.; Magid, R.; Shipley, J.; Senior, R. Targeted Disruption of the Matrix Metalloproteinase-9 Gene Impairs Smooth Muscle Cell Migration Arterial Remodeling and Geometrical. Circulation Research 2002, 91, 852-859.] Therefore, it is of great importance to develop a material which is able to specifically guide the selective adhesion and directional migration of ECs rather than other cells, toward disease site to regenerate tissues and restore their functions. Besides, since natural ECs are migrating much slower than many other cells such as SMCs and fibroblasts, it is also very important to use materials to selectively accelerate the migration speed of ECs, to achieve faster regeneration.

Bioactive molecules that possess or enriches signals have been implemented to otherwise inert materials to enhance the adhesion of ECs, such as extracellular matrix proteins and their derived peptides, growth factors, and other bioactive molecules such as heparin and polydopamine. However, the majority of the materials are not cell-selective. Only a few studies have recently demonstrated that immobilization of an EC-specific ligand onto a cytocompatible matrix can specifically promote EC adhesion, and may help the regeneration of endothelium. [Yang, Z.; Tu, Q.; Wang, J.; Huang, N. The Role of Heparin Binding Surfaces in the Direction of endothelial and Smooth Muscle Cell Fate and Re-endothelialization. Biomaterials 2012, 33, 6615-6625.de Mel, A.; Jell, G.; Stevens, M.; Seifalian, A. Biofunctionalization of Biomaterials for Accelerated in Situ endothelialization: A review, Biomacromolecules 2008, 9, 2969-2979.] Since the number of circulatory ECs and EC-precursor cells are limited in blood, the process of generating a complete layer of ECs on injured locus by selective adhesion is allowed to occur naturally, would have been a slow and inefficient process. Furthermore, it is well acknowledged that selective adhesion per se does not contribute to directional migration or enhanced cell mobility, which would have constituted another approach to promote the generation or regeneration of an intact EC s layer.

Gradient materials, which have a gradually varying physical or chemical signal density, have proved to be powerful tools for accelerating cell migration. More importantly, gradient signals can guide cells to move to a preferred direction with higher signal density. Therefore, a gradient provides another possible solution to regenerate endothelium by inducing the ECs from surround healthy tissue to migrate and settle upon the gradient material. However, the lack of cell selectivity in these type of materials remains a problem. On one hand, a gradient material can induce the directional migration of many types of cells, i.e. it guides all types of cells to the same direction indiscriminately. On the other hand, traditional protein/peptide density gradient material can enhance the migration rate of different cells to a similar extent. For example, a gelatin density gradient can enhance the migration rates of both ECs and SMCs. [Yu S, Mao Z, Gao C. Preparation of gelatin density gradient on poly(ε-caprolactone) membrane and its influence on adhesion and migration of endothelial cells[J]. Journal of Colloid & Interface Science, 2015, 451:177-183.] As a result, SMCs still move much faster than ECs, defeating the purpose of enriching ECs relative to SMCs and making gelatin density gradient unfit for endothelium regeneration.

Our previous study has been the only study to fabricate two complementary density gradients of hydrophilic poly (2-hydroxyethyl methacrylate) (PHEMA) brushes and YIGSR (SEQ ID NO: 8) peptide, an amino acids sequence specifically improving the mobility of ECs. In that design, the gradient material was generated on a silicon wafer/glass slide using a surface-initiated atom transfer radical polymerization (SI-ATRP) approach. ECs exhibited preferred orientation and enhanced directional migration toward the region of lower PHEMA density and higher YIGSR (SEQ ID NO: 8) density. [Ren, T.; Yu, S.; Mao, Z.; Enrique Moya, S.; Han, L.; Gao, C. Complementary Density Gradient of Poly(hydroxyethyl methacrylate) and YIGSR (SEQ ID NO: 8) Selectively Guides Migration of Endotheliocytes. Biomacromolecules 2014, 15, 2256-2264.] However, that study has several drawbacks. 1) Although a setup based on SI-ATRP is robust on model surfaces such as silica, the process for generating two complementary gradients is complicated, leading to inconvenience when adopting real biomaterials such as degradable biomaterials. 2) Two complementary gradients must work together to achieve directional cell migration. The structure control of the complementary gradients may be compromised due to the mismatch of the molecular size of the two components. 3) The antifouling effect of the complementary gradient becomes weaker with reduced density of the hydrophilic polymer on one end of the gradient, thus leads to unpredictable behavior of cells on these positions. Furthermore, the cell repelling effect of common hydrophilic polymer is insufficient to achieve long-term rejection of cells. 4) Although the directional migration of ECs was achieved by this gradient, the adhesion of other cells cannot be prevented because the complementary gradient has limited effect on cell resist due to low density of hydrophilic polymer on half of the gradient. Since other cells, such as SMCs and fibroblasts, are much higher in number compared to ECs in natural environment such as damaged vessel, the other cells can attach to the gradient, occupy the position and prevent further migration of ECs. This is also not good for correct endothelium regeneration.

Thus, there remains a need for material that is capable of inducing selective adhesion and directional migration of endothelial cells, and preferably a bioactive material that is inexpensive, sterile, stable, non-immunogenic, and easy to synthesize and be affixed or applied onto a variety of media.

SUMMARY OF THE INVENTION

Therefore, the present invention disclosed a two-layer gradient coating structure, adaptable to be applied onto degradable biomaterials, and to achieve selective adhesion and subsequent directional migration of ECs. The first layer is a uniform cell-resisting polymer, i.e. antifouling polymers that can repel 80% or more of non-endothelial cells from adhering to the first layer within at least 72 h in static culture condition. A concentration gradient of peptides that can specifically bind to ECs were subsequently applied onto the cell-resistant first layer to form a second layer. The two-layer gradient coating structure induces selective adhesion and directional migration for endothelial cells. This gradient coating is easy to manufacture and sterilize, inexpensive, non-immunogenic, and has long lasting stability and effectiveness. When implanted onto point of injury in blood vessels or artificial blood vessels, the gradient coating on degradable biomaterials can accelerate the regeneration of endothelium and prevent thrombosis.

In one embodiment, a gradient coating article configured to induce selective adhesion and directional migration of endothelial cells is provided. The article includes a first layer of cell-resisting polymers that repels cell adhesion nondiscriminatory; and a second layer of peptides having specific affinity to, and operable to interact specifically with, endothelial cells, wherein the peptides are distributed in a concentration gradient configured to induce the endothelial cells to migrate towards the direction of increased peptide concentration at a rate that is higher than smooth muscle cells, and wherein the second layer is covalently linked to the second layer.

In one embodiment, the gradient coating article is operable to repel at least 80% of non-endothelial cells and induce the adhesion of substantially all endothelial cells.

In one embodiment, the gradient coating article is operable to induce the directional migration of over 80% of endothelial cells, while exerting no impact on random migration of non-endothelial cells.

In one embodiment, the gradient coating article is operable to induce the directional migration of the endothelial cells at a rate higher than when there is no gradient.

In one embodiment, the first layer of cell-resisting polymers comprises an evenly distributed polymer brushes of single polymer molecular thickness.

In one embodiment, the second layer of peptides is a single molecular layer.

In one embodiment, the first layer of cell-resisting polymers is linked to the second layer of peptides via conjugation by Michael addition reaction.

In one embodiment, the Michael addition reaction is between thiol group and carbon double bond.

In one embodiment, the cell-resisting polymers are selected from the following group: methacrylic anhydride modified hyaluronic acid with the molecular weight in the range of 500-200000 Da, and polyphosphoric acid choline with the molecular weight in the range of 500-200000 Da.

In one embodiment, the cell-resisting polymers have one end functionalized with a carboxyl group and have double bonds within repeating units.

In one embodiment, the peptides are selected from the following group: Cys-Cys-Ala-Gly (SEQ ID NO: 3), Cys-Cys-Asn-Gly (SEQ ID NO: 4), Cys-Cys-Thr-Gly (SEQ ID NO: 5), Cys-Gly-Tyr-Leu (SEQ ID NO: 2), Cys-Ser-Val-Val-Tyr-Gly-Leu-Arg (SEQ ID NO: 6), Cys-Arg-Glu-Asp-Val (SEQ ID NO: 1).

In one embodiment, the thickness of the first layer of cell-resisting polymers is in the range of 0.5-5 nm.

In one embodiment, the thickness of the second layer of peptides is in the range of 0.5-5 nm.

In one embodiment, the gradient coating article further includes a substrate comprising biocompatible biodegradable polymers.

In one embodiment, an implantable article is provided that is configured to promote selective adhesion of endothelial cells and directional migration of the endothelial cells. The implantable article includes: a first layer of cell-resisting polymers that is uniform in composition and repels cell adhesion nondiscriminatory; a second layer of peptides having specific affinity to, and operable to interact specifically with, endothelial cells, wherein the peptides are distributed in a concentration gradient configured to induce the endothelial cells to migrate towards the direction of increased peptide concentration; and a substrate layer comprising biocompatible biodegradable polymers.

In one embodiment, the implantable article is configured so that the endothelial cells migrate towards the direction of increased peptide concentration at a speed greater than that of smooth muscle cells.

In one embodiment, the first layer and the second layer of the implantable article are covalently linked.

In one embodiment, the first layer of cell-resisting polymers within the implantable article is an evenly distributed polymer brushes of single polymer molecular thickness, wherein the peptides are selected from the following group:

Cys-Cys-Ala-Gly, (SEQ ID NO: 3)

Cys-Cys-Asn-Gly, (SEQ ID NO: 4)

Cys-Cys-Thr-Gly, (SEQ ID NO: 5)

Cys-Gly-Tyr-Leu, (SEQ ID NO: 2)

Cys-Ser-Val-Val-Tyr-Gly-Leu-Arg, (SEQ ID NO: 6)

Cys-Arg-Glu-Asp-Val. (SEQ ID NO: 1)

In one embodiment, the gradient coating article is operable to form a part of an artificial blood vessel or stent to accelerate endothelium regeneration.

In one embodiment, a method for using peptide gradient to induce selective adhesion and directional migration of endothelial cells is provided. The method includes the of providing a first layer of cell-resisting polymers that repels cell adhesion nondiscriminatory; providing a second layer of peptides having specific affinity to and operable to interact specifically to endothelial cells, wherein the peptides are distributed in a concentration gradient along one axis and are conjugated to the cell-resisting polymers via a Michael addition reaction to form a two-layer structure; and placing the two-layer structure in a place accessible to endothelial cells and allow endothelial adhesion and migration to occur.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

ADVANTAGES OF THE INVENTION

Advantages of this disclosure are as follows: 1) For the first time, selective adhesion and directional migration of ECs were coupled and simultaneously achieved on the gradient coating, with enhanced mobility for ECs. The result is surprising considering the relatively succinct design. 2) The gradient coating can selectively induce the directional migration of ECs from surround tissue to wound area, in addition to capturing circulatory ECs and EC precursor cells, leading to more efficient regeneration of intact endothelium on injured blood vessel or artificial vessels. 3) The two-layer structure, including one uniform layer and one gradient layer, imparts better cell-resisting effect to non-endothelial cells and subsequent better selective cell adhesion of ECs, and is more robust to prepare since the structure can be easily tuned and characterized. 4) The uniform cell-resisting polymer layer repels all cells; whereas the gradient peptide layer attracts only endothelial cells. Acting concertedly, the two-layer structure selectively promotes the adhesion of ECs only and directional migration of ECs along the concentration gradient. 5) The presence of the peptide concentration gradient, in combination of cell resisting effect of the uniform layer, enhances the migration speed or the mobility of ECs. 6) The gradient coating can be applied onto artificial vessels made of degradable biomaterials, resulting in 100% regeneration of endothelium within 7 days and the prevention of thrombosis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
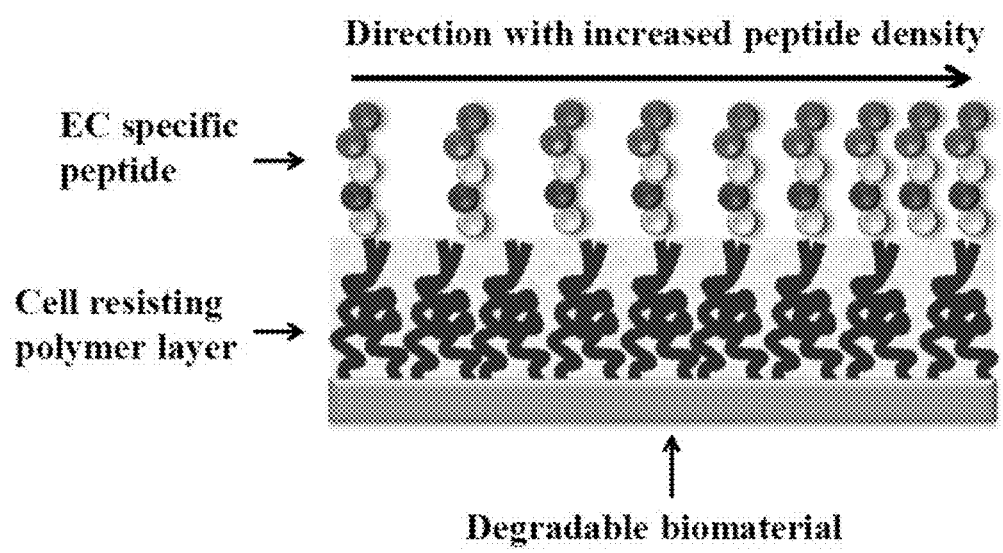
FIG. 1 is schematic illustration showing the two layer structure of the gradient coating on a degradable biomaterial substrate, in accordance with certain embodiments.
Figure 2:
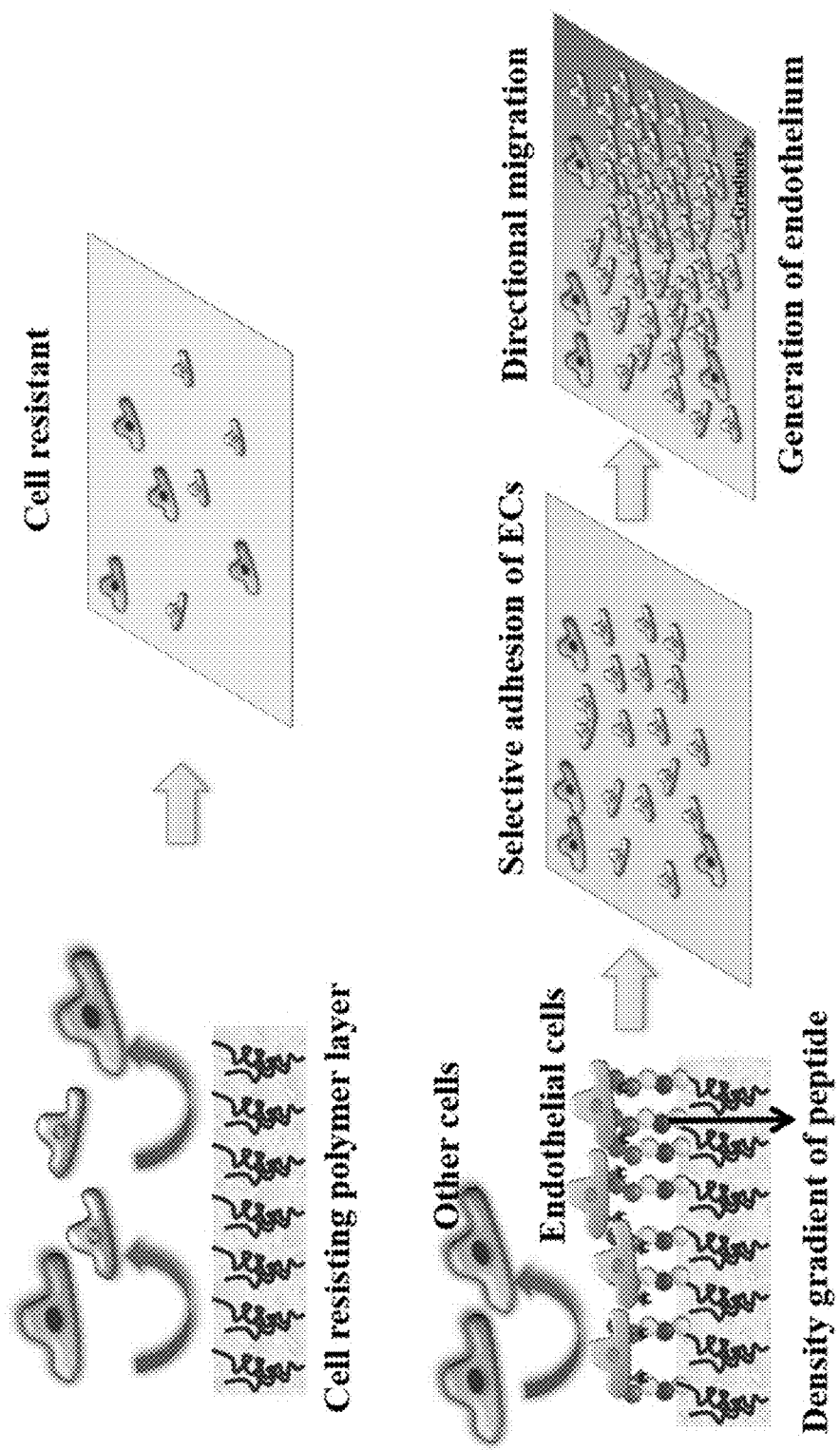
FIG. 2 is a schematic illustration showing the cell-repulsion effect of a cell-resisting polymer layer as well as selective adhesion and directional migration of ECs induced by the gradient coating, in accordance with certain embodiments.

It is to be understood that certain descriptions of the present invention have been simplified to illustrate only those elements and limitations that are relevant to a clear understanding of the present invention, while eliminating, for purposes of clarity, other elements. Those of ordinary skill in the art, upon considering the present description of the invention, will recognize that other elements and/or limitations may be desirable in order to implement the present invention. However, because such other elements and/or limitations may be readily ascertained by one of ordinary skill upon considering the present description of the invention, and are not necessary for a complete understanding of the present invention, a discussion of such elements and limitations is not provided herein. As such, it is to be understood that the description set forth herein is merely exemplary to the present invention and is not intended to limit the scope of the claims.

Other than in the examples herein, or unless otherwise expressly specified, all of the numerical ranges, amounts, values, and percentages, such as those for amounts of materials, elemental contents, times and temperatures of reaction, ratios of amounts, and others, in the following portion of the specification and attached claims may be read as if prefaced by the word "about," even though the term "about" may not expressly appear with the value, amount, or range. Accordingly, unless indicated to the contrary, the numerical parameters set forth in the following specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains error necessarily resulting from the deviation found in its underlying respective testing measurements. Furthermore, when numerical ranges are set forth herein, these ranges are inclusive of the recited range end points (i.e., end points may be used). Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

Certain compositions within the present invention are generally described in the form of biopolymers for use in medical and biological systems. It will be understood, however, that the present invention may be embodied in forms and applied to end uses that are not specifically and expressly described herein. For example, one skilled in the art will appreciate that compositions and methods comprising plastics have application in many industries, as well as the medical arts.

All patents, publications, or other disclosure material referenced herein are incorporated by reference in their entirety. Any patent, publication, or other disclosure material, in whole or in part, that is incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The articles "a," "an," and "the" are used herein to refer to one or more than one (i.e., to at least one) of the grammatical objects of the article. By way of example, "a component" means one or more components, and thus, possibly, more than one component is contemplated and may be employed or used.

The term "polypeptide", and the terms "protein" and "peptide" which are used interchangeably herein, refers to a polymer of amino acids.

The term "polymer," as used herein, refers to natural and synthetic molecules with repeating structural units including, but not limited to, molecules comprising gels and plastics.

The term "biocompatible" refers to the absence of stimulation of a severe, long-lived or escalating biological response to an implant or coating, and is distinguished from a mild, transient inflammation which typically accompanies surgery or implantation of foreign objects into a living organism.

The term "degradable biomaterial" refers to biocompatible materials that are degradable within a live organism including a human being. Examples of degradable biomaterial include, but are not limited to, polylactic acid (PLA), polyglycolic acid (PGA), polylactic-co-glycolytic acid (PLGA), polycaprolactone, and copolymers thereof, polyesters, such as polyglycolides, polyanhydrides, polyacrylates, polyalkyl cyanoacrylates, such as n-butyl cyanoacrylate and isopropyl cyanoacrylate, polyacrylamides, polyorthoesters, polyphosphazenes, polypeptides, polyurethanes, polystyrenes, polystyrene sulfonic acid, polystyrene carboxylic acid, polyalkylene oxides, alginates, agaroses, dextrins, dextrans, and polyanhydrides.

A "gradient" is one or more dimensions in space along which the concentration and/or accessibility of one or more substances may vary. Concentration gradients include both linear gradients (i.e., gradients which increase or decrease at a continuous rate) and non-linear gradients.

The present invention provides a gradient coating which, when applied a medium or standing alone, can cause selective adhesion and directional migration of ECs, which can be used to support the regeneration of the endothelium on artificial vessel or implant stent. The medium includes the surfaces of degradable biomaterial, a film, a medical device, or a tissue, or a layer of cells.

The gradient coating comprises a two-layer structure, in which the lower layer is consist of certain specific cell-resisting polymers and the upper layer is consist of density gradient of peptides which is able to selectively interact with ECs. The gradient coating can induce the selective adhesion of ECs and subsequently direction migration toward +X direction of the gradient, said +X direction of the gradient is the direction with enhanced peptide density.

In some embodiments, a uniformly distributed single molecular thick cell-resisting polymer layer is provided to repel cells, i.e., to provide an anti-cell adhesion function that prevent adhesion of non-targeted cells such as SMCs. Preferably, the cell-resisting polymer is selected from following polymers: methacrylicanhydride modified hyaluronic acid (MA-HA) and polyphosphoric acid choline, with the molecular weight in the range of 500-200000 Da. These polymers can be synthetic, derived from natural extracellular matrix, or both. One example of the cell-resisting polymer is hyaluronic acid (HA), a natural polysaccharide that widely used in medical applications due to its superior inert properties as an anionic glycosaminoglycan and high anti-fouling ability against fibronectin adsorption. Therefore, the MA-HA layer functions to resist non-selective cell adhesion. In some embodiments, only one single molecular layer with the thickness within 0.5-5 nm of the cell-resisting polymer is enough to achieve satisfactory cell-resist effect. The cell-resisting polymers contain carboxyl group and double bond in their repeating unit, feasible for the reaction with amino group functionalized substrate and thiol group functionalized peptide, respectively.

In some embodiments, thiol (cysteine)-functionalized peptide which can specifically interact with ECs was conjugated onto the cell-resisting polymer layer containing double bonds via a Michael addition reaction, a high efficiency reaction, in a gradient manner to form the density gradient of peptides. In some embodiments, the peptides are selected from following sequences: Cys-Cys-Ala-Gly (SEQ ID NO: 3), Cys-Cys-Asn-Gly (SEQ ID NO: 4), Cys-Cys-Thr-Gly (SEQ ID NO: 5), Cys-Gly-Tyr-Leu (SEQ ID NO: 2), Cys-Ser-Val-Val-Tyr-Gly-Leu-Arg (SEQ ID NO: 6), Cys-Arg-Glu-Asp-Val (SEQ ID NO: 1). In a preferred embodiment, a Cys-Arg-Glu-Asp-Val (CREDV) (SEQ ID NO: 1) peptide is used, which is the smallest active sequence of fibronectin that is recognized by and interacts with integrin $\alpha_4\beta_1$ receptor on ECs and has been widely used for designing EC-selective surfaces. In come embodiments, a single layer peptide with the thickness in the range of 0.5-5 nm is provided. These peptides are synthetic, very short sequence with low cost, relatively easy to manufacture and stable in their application, compared to expensive and unstable proteins/growth factors. In addition, the small size of the peptide allows refined tunable binding density on the cell-resisting polymer layer, leading to excellent control of the density gradient of the peptide.

With the presence of cell-resisting polymer layer, over 80% of cells are repelled or rejected from the polymer surface, preventing them from strong adhesion. The said gradient coating can support the adhesion of ECs, but cannot support the adhesion of other cells such as SMCs and fibroblasts. Besides, the gradient coating also can induce the directional migration of ECs, with over 80% of ECs continuously move toward the direction with enhanced peptide density. Meanwhile the gradient coating has no influence on the random movements of other cells. The gradient coating also enhances the migration rate of ECs, as a result the ECs have a higher migration rate gradient coating on the compared to that of SMCs.

In some embodiments, a gradient material, which can induce selective adhesion and directional migration of ECs, was generated by covalently immobilizing said gradient coating onto a degradable biomaterial with amino groups on its surface, in the presence of a proper crosslinking agent. The obtained gradient material can induce the selective adhesion of ECs and subsequently direction migration toward +X direction of the gradient, with enhanced peptide density.

An implantable material, which contains the above mentioned gradient material, can be generated and used for artificial blood vessel or stent.

A method to prepare the gradient materials which can selectively control the adhesion and directional migration of ECs, said method includes following steps: 1) Prepare cell-resisting polymer solution and covalently conjugate the cell-resisting polymer onto substrate, said substrate is biocompatible biodegradable polymers. 2) Prepare peptide solution and gradually conjugate onto the cell-resisting polymer layer with covalent bonding to form a concentration gradient of peptide, said peptide is able to selectively interact with ECs. As a result, said gradient material which can induce selective adhesion of ECs and subsequently direction migration toward +X direction of the gradient, said +X direction of the gradient is the direction with enhanced peptide density.

The following examples are intended to more clearly illustrate aspects of the invention, but are not intended to limit the scope thereof.

Example I

Synthesis of Methacrylatedhyaluronic Acid (MA-HA)

Figure 3:
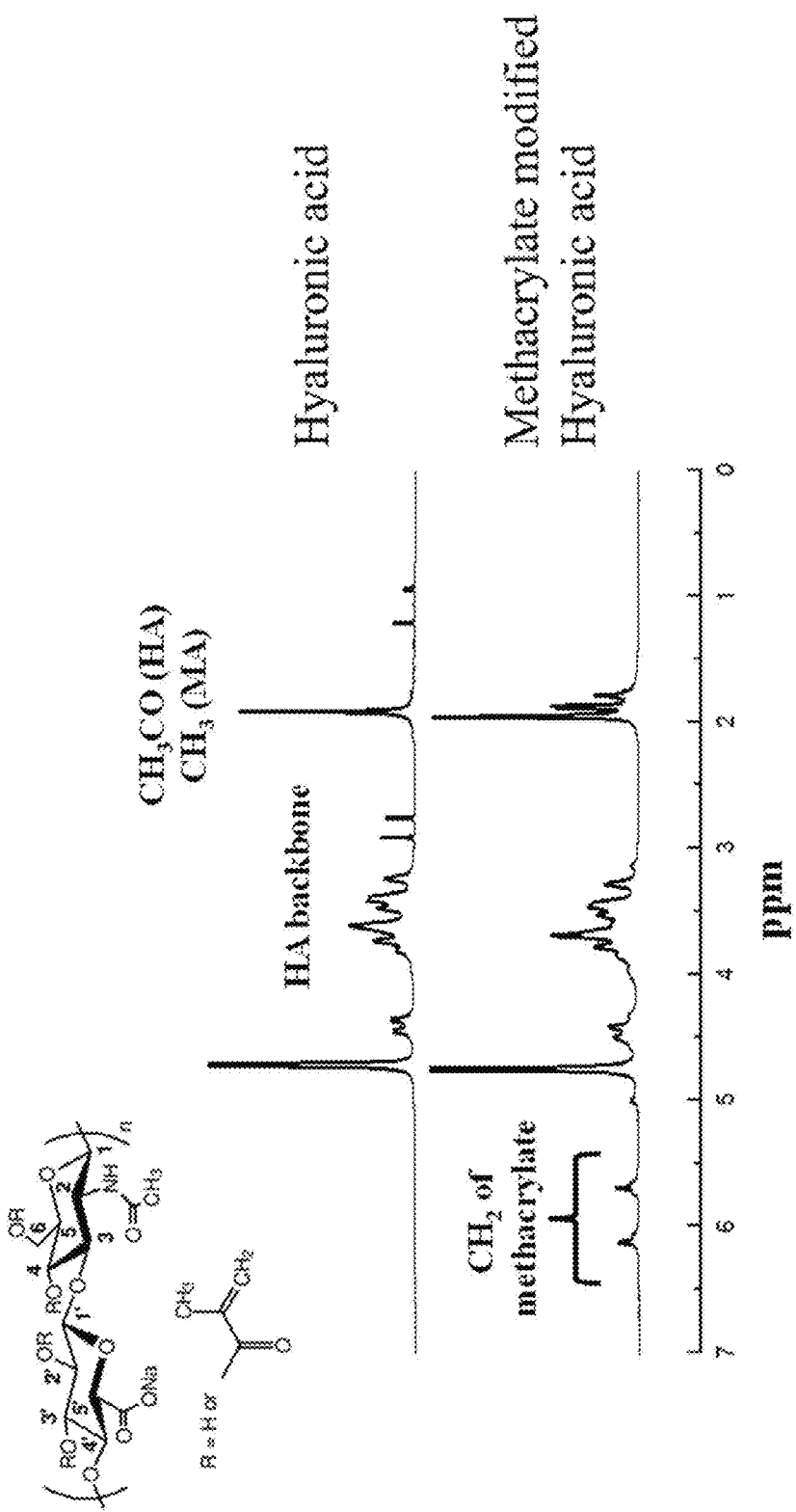
FIG. 3 is a graph showing $^1$H NMR results of hyaluronic acid and methacrylate modified hyaluronic acid in the cell-resisting layer, in accordance with certain embodiments.
Figure 4:
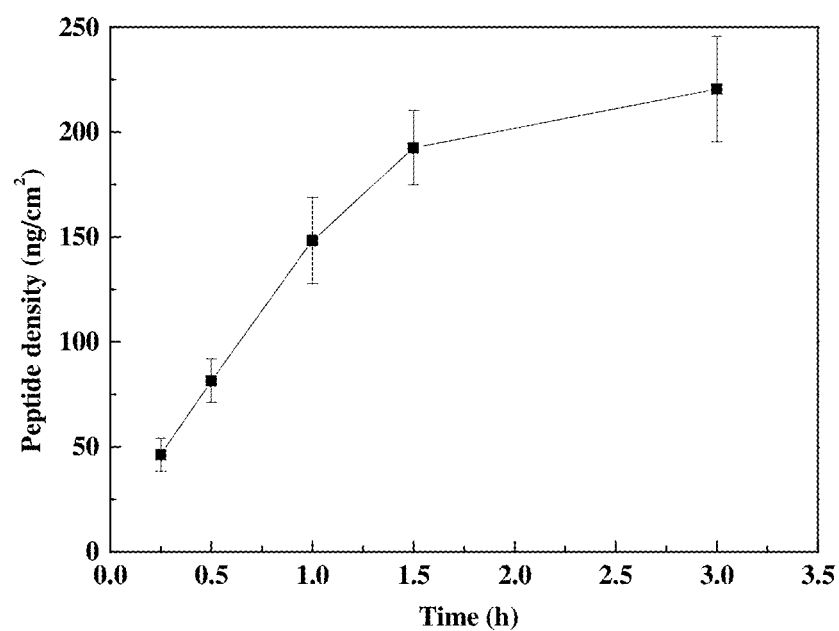
FIG. 4 is a graph showing peptide density on uniform CREDV (Cys-Arg-Glu-Asp-Val) (SEQ ID NO: 1) surface as a function of thiol-ene reaction time, in accordance with certain embodiments.
Figure 5:
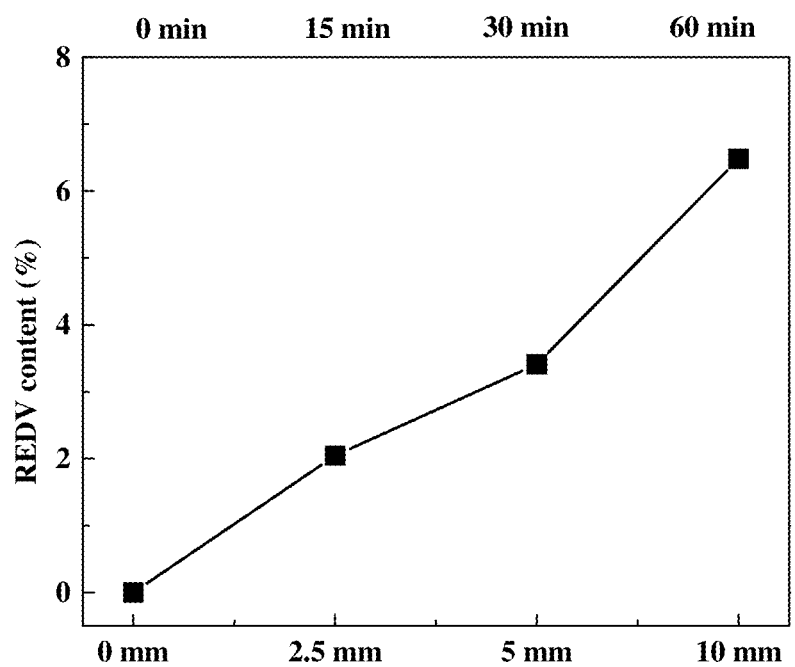
FIG. 5 is a graph showing molar ratio between CREDV (SEQ ID NO: 1) peptide to the repeating unit of MA-HA at different positions on the gradient surface, in accordance with certain embodiments. The result provides direct evidence of the successful generation of peptide concentration gradient.

MA-HA was prepared according to a previously reported method. [Bae, M.; Yang, D.; Lee, J.; Heo, D.; Kwon, Y.; Youn, I. Photo-cured Hyaluronic Acid-Based Hydrogels Containing Simvastatin as a Bone Tissue Regeneration Scaffold. Biomaterials 2011, 32, 8161-8171.] In brief, HA (1.0 g) was dissolved in 100 mL mixed solvent of DMF/water (1/2, v/v), into which a 20-fold excess of methacrylic anhydride (7.4 mL) was added. The mixture was stirred for 24 h in an ice bath after the solution pH was adjusted to 8.0 using a 5 M NaOH solution. The pH was maintained between 8-9 during the whole procedure. MA-HA was obtained by precipitation in excess ethanol and collected by centrifugation, which was further purified by dialysis for 3 d against distilled water, and finally freeze-dried. The grafting ratio of methacrylate was 2.1 in each HA repeating unit with four —OH reaction sites according to $^1$H NMR (Figure. 3).

Preparation of Polydopamine (PDA) Coated PCL Substrate

PCL membrane was prepared by spin-coating a 2% (w/v) PCL/1,4-dioxane solution onto the glass slides under 1600 rpm. The PCL membranes were immersed in a 2 mg/mL dopamine/tris-HCl (10 mM, pH=8.5) solution at 37° C. After a 12 h deposition, the PDA-coated PCL membranes were washed with water.

Grafting of MA-HA

MA-HA molecules were immobilized onto the surface of the PCL-PDA substrate via a condensation reaction between —COOH of MA-HA and —NH$_2$ of PDA under the presence of 1-ethyl-3-(3-dimethylaminopropyl)-carbodiimide hydrochloride and N-hydroxysuccinimide (EDC/NHS). In brief, 200 mg MA-HA, 7 mg EDC and 12 mg NHS were dissolved in 100 mL water, and its pH value was adjusted to 5.5, in which the PDA-coated PCL membranes were incubated at 37° C. for 3 h, followed by washing with plenty of water.

Grafting of CREDV Peptides

Thiol-functionalized CREDV (SEQ ID NO: 1) peptides were dissolved in Na$_2$CO$_3$/NaHCO$_3$ buffer (pH=9) to reach a concentration of 0.4 mg/mL. The MA-HA-coated PCL membranes were immersed into the CREDV (SEQ ID NO: 1) solution at 37° C. for different times. To generate an CREDV (SEQ ID NO: 1) concentration gradient (total length was 10 mm), the CREDV (SEQ ID NO: 1) solution was slowly injected into a centrifuge tube by a micro-infusion pump (WZS-50F2 from Zhejiang University Medical Instrument, Hangzhou, China) at 37° C., where MA-HA-coated PCL membranes were placed vertically. The injection rate was adjustable with the longest reaction time of 60 min.

Cell Adhesion Assay

The co-culture of ECs and smooth muscle cells was implemented by seeding $2.1 \times 10^4$/cm$^2$ of each type of cell in a 1:1 mixture of RPMI-1640 and DMEM. ECs and Smooth muscle cells were stained with 5 mg/mL 3,3'-dioctadecyloxacarbocyanine perchlorate (DiO, green) and 1,1'-dioctadecyl-3,3,3',3'-tetramethyl indocarbocyanine perchlorate (DiL, red), respectively, for 5 min before seeding.

Figure 6:
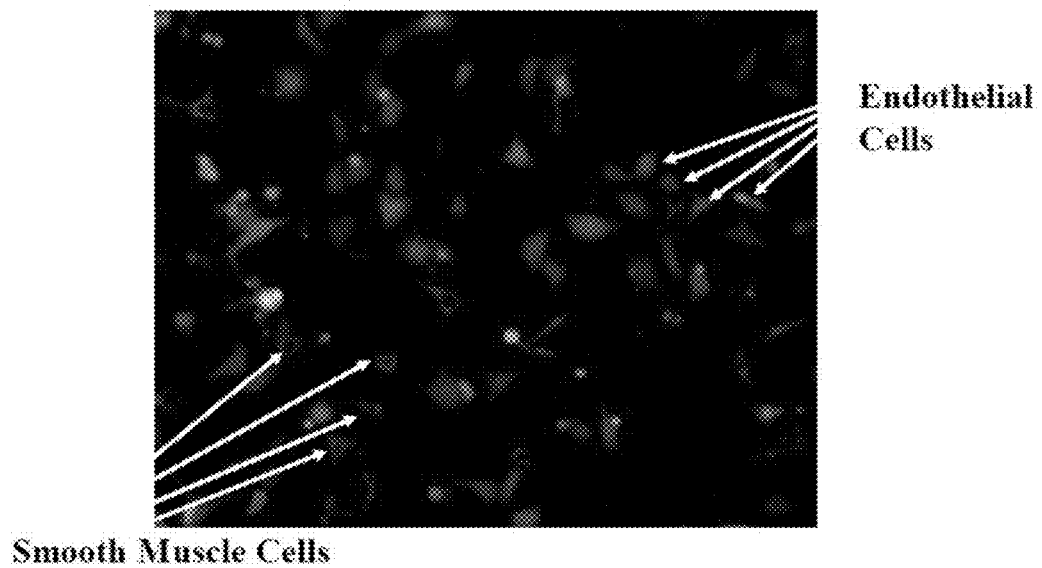
FIG. 6 is a graph showing representative fluorescent images of ECs (green) and smooth muscle cells (red) on CREDV (SEQ ID NO: 1) peptide concentration gradient in accordance with certain embodiments.
Figure 7:
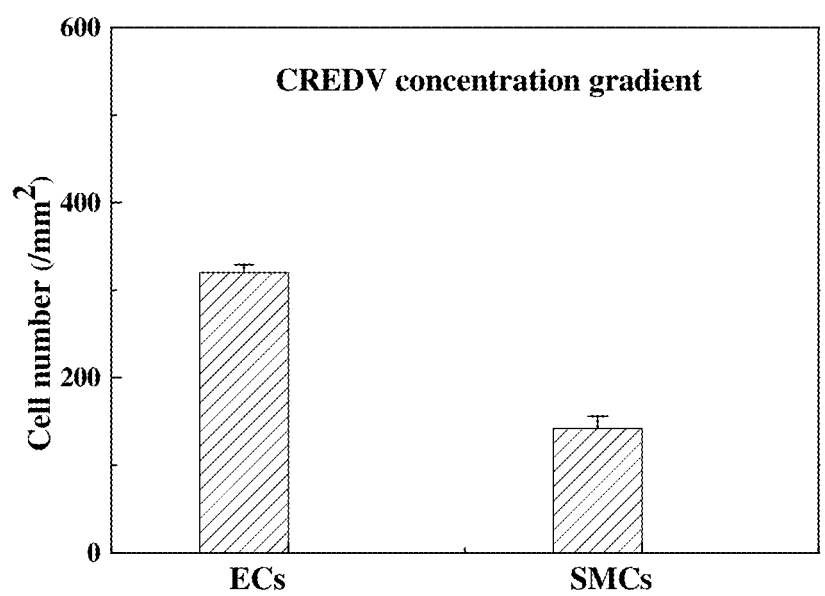
FIG. 7 is a graph showing numbers of ECs and smooth muscle cells cultured for 8 hours on CREDV (SEQ ID NO: 1) concentration gradient, in accordance with certain embodiments. The quantitative result indicated that much more ECs adhered on the gradient coating compare to SMCs, proving the selective adhesion of ECs.
Figure 8:
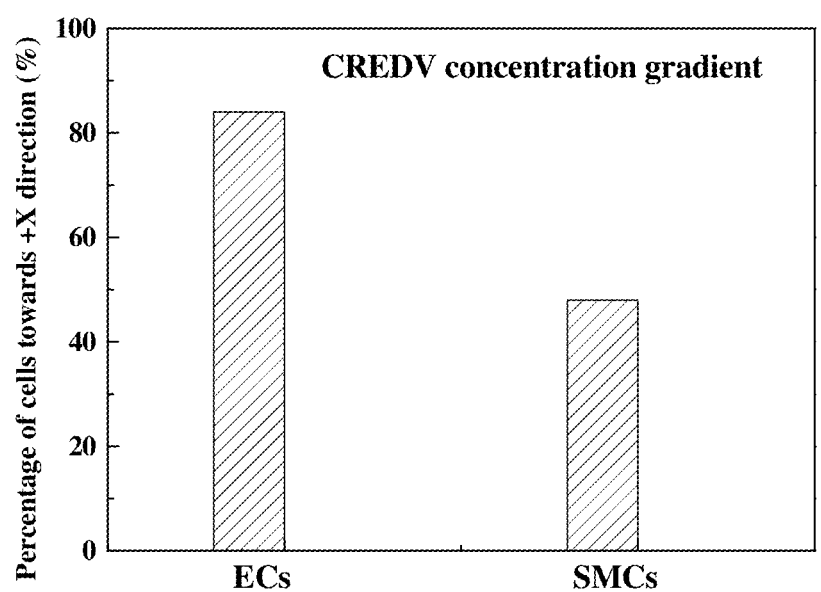
FIG. 8 is a graph showing percentage of ECs or smooth muscle cells migrating towards +X direction on CREDV (SEQ ID NO: 1) concentration gradient, in accordance with certain embodiments. The result proved the selective directional migration of ECs was achieved by the gradient coating.
Figure 9:
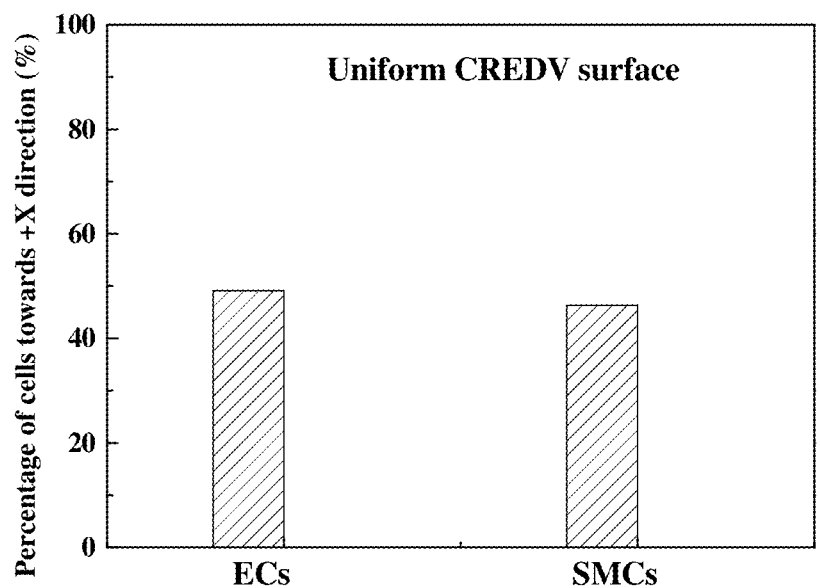
FIG. 9 is a graph showing percentage of ECs or smooth muscle cells migrating towards +X direction on uniform CREDV (SEQ ID NO: 1) peptide surface with MA-HA, in accordance with certain embodiments. The result indicated that the uniform peptide surface cannot guide directional migration of ECs.
Figure 10:
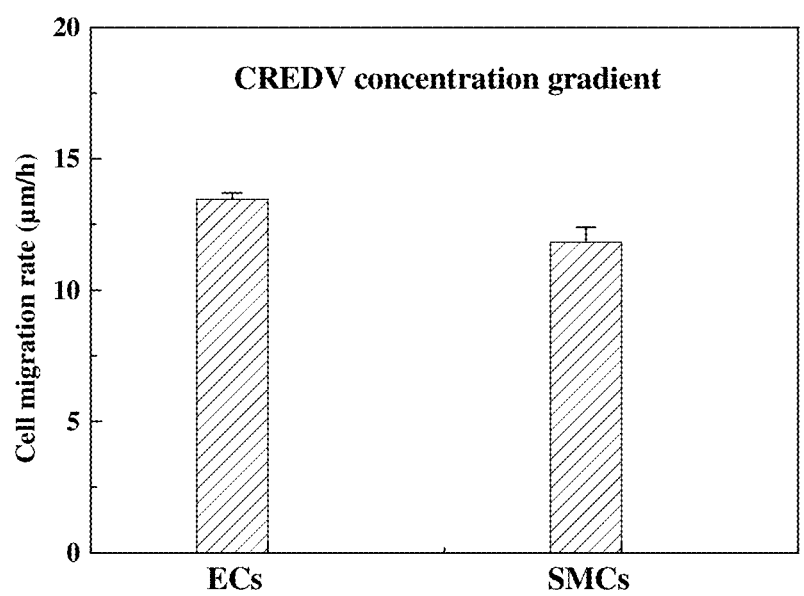
FIG. 10 is a graph showing migration rate of ECs and smooth muscle cells on CREDV (SEQ ID NO: 1) concentration gradient, in accordance with certain embodiments. Compare with the result in FIG. 11, it clearly indicated that the migration rate of ECs was significantly enhanced by the gradient coating.

As shown in FIGS. 6 and 7, the number of ECs was approximately 2.5 folds of that of smooth muscle cells on the whole CREDV (SEQ ID NO: 1) concentration gradient, indicating the selective cell adhesion effect achieved by gradient coating.

Cell Migration Assay

The respective uniform surfaces with the same reaction time and thereby the same CREDV (SEQ ID NO: 1) peptide concentrations were used as controls. ECs and smooth muscle cells were seeded at a density of $5 \times 10^3$/cm$^2$ and allowed to attach for 12 h. Cell migration traces were recorded in situ for 12 h under a time-lapse phase-contrast microscope equipped with a cell culture chamber (37° C. and 5% $CO_2$ humidified atmosphere). The starting position of each single cell was automatically defined as the original position (0, 0). The cell migration distance S was then calculated by the Chemotaxis Tool (Ibids, Germany) according to the following equation.

$$S=\Sigma_{i=1}\sqrt{(x_i-x_{i-1})^2+(y_i-y_{i-1})^2} \quad (1)$$

The cell migration rate was calculated base on the formula v=S/t. [Han, L.; Mao, Z.; Wu, J.; Guo, Y; Ren, T.; Gao, C. Directional Cell Migration through Cell-cell Interaction on Polyelectrolyte Multilayers with Swelling Gradients. Biomaterials 2013, 34, 975-984.]

As shown in FIGS. 8 and 9, 84% of the ECs moved toward the higher CREDV (SEQ ID NO: 1) peptide concentration of the gradient, which is much higher than smooth muscle cells. On uniform surface, both around 50% ECs and smooth muscle cells migrated towards +X direction. The results proved the selective directional migration of ECs was achieved by the gradient coating.

As shown in FIGS. 10 and 11, the migration rate of smooth muscle cells slowed down slightly (11.8 μm/h). On CREDV (SEQ ID NO: 1) peptide concentration gradient, endothelial cells migrated faster than smooth muscle cells. The results clearly indicated that the migration rate of ECs was significantly enhanced by the gradient coating.

As shown in FIG. 12, after being cultured for 72 h, number of ECs was almost 5-times to smooth muscle cells on CREDV (SEQ ID NO: 1) concentration gradient. The results indicate the continuous increase of ECs on the gradient coating as a result of combinational effect of selective adhesion and directional migration, while the number of SMCs was still very low.

Comparing Example I

Grafting of MA-HA was carried out according to Example 1. No CREDV (SEQ ID NO: 1) peptide was further immobilized.

Cell adhesion and migration assays were carried out according to Example 1.

As shown in FIG. 13, the cell adhesion number of ECs and smooth muscle cells was similar on MA-HA surface, which was much lower than ECs on CREDV (SEQ ID NO: 1) concentration gradient. The results suggested the universe cell-resisting effect to both ECs and SMCs of HA layer.

As shown in FIG. 14, both around 50% of ECs and smooth muscle cells migrated towards +X direction. ECs showed no directional migration on MA-HA surface. The result indicated that the cell-resisting layer do not have ability to induce directional migrating of both ECs and SMCs.

As shown in FIG. 15, migration rate of ECs (7 μm/h) was much lower compared to CREDV (SEQ ID NO: 1) concentration gradient (14 μm/h). The result also indicated that SMCs move much faster than ECs on cell-resisting layer, which is similar to the pattern in natural environment.

As shown in FIG. 16, after being cultured for 72 h, the number of ECs and smooth muscle cells on MA-HA surface was similar, which was only ¼ of the number of ECs on CREDV (SEQ ID NO: 1) concentration gradient. Together with FIG. 13, the results suggested the long termcell-resisting effect to both ECs and SMCs of HA layer.

Comparing Example II

To generate an CREDV (SEQ ID NO: 1) concentration gradient (total length was 10 mm) without cell-resisting layer, the CREDV (SEQ ID NO: 1) solution was slowly injected into a centrifuge tube by a micro-infusion pump at 37° C., where PDA-coated PCL membranes were placed vertically, The injection rate was adjustable with the longest reaction time of 60 min. As a result, a CREDV (SEQ ID NO: 1) concentration gradient without MA-HA, the cell-resisting layer, was fabricated.

Cell adhesion and migration assays were carried out according to Example 1.

As shown in FIG. 17, on CREDV (SEQ ID NO: 1) peptide concentration gradient without MA-HA, the number of smooth muscle cells was much higher than that on CREDV (SEQ ID NO: 1) concentration gradient. The result indicated that the peptide concentration gradient can support both ECs and SMCs adhesion without the HA cell-resisting layer.

As shown in FIG. 18, on CREDV (SEQ ID NO: 1) peptide concentration gradient without MA-HA, 70% of ECs migrated towards +X direction, which was much lower than on CREDV (SEQ ID NO: 1) concentration gradient with MA-HA.

As shown in FIG. 19, migration rate of ECs on CREDV (SEQ ID NO: 1) concentration gradient without MA-HA was much lower than smooth muscle cells. The result indicated that peptide concentration gradient alone can selectively induce directional migration of ECs to some extent, but the effect is smaller than gradient coating (FIG. 8).

As shown in FIG. 20, after being cultured for 72 h, the number of ECs was similar to that of smooth muscle cells, which showed no cell selectivity.

Comparing Example III

A complimentary gradient coating with HA and REDV (SEQ ID NO: 1) peptide was generated and compared, in according to [Ren, T.; Yu, S.; Mao, Z.; Enrique Moya, S.; Han, L.; Gao, C. Complementary Density Gradient of Poly (hydroxyethyl methacrylate) and YIGSR Selectively Guides Migration of Endotheliocytes. Biomacromolecules 2014, 15, 2256-2264.]

A PDA coated PCL membrane, prepared according to example I, was vertically placed in a cylindrical plastic container, into which the HA solution with the presence of EDC/NHS was injected continuously by a micro infusion pump at room temperature with a rate of 2 mL/h. A total of 3 h later, the membrane with HA concentration gradient was taken out and washed with plenty of water. The membrane was then immersed in a glutaraldehyde solution to react with residual amino groups and change them to aldehyde group. After thoroughly washing in plenty of water, the membrane was immersed into a CREDV (SEQ ID NO: 1) solution to generate a complimentary concentration gradient of peptide.

Cell adhesion and migration assays were carried out according to Example 1.

As shown in FIG. 21, the results showed that the complimentary gradient can partially reject both ECs and SMCs adhesion to similar extent. But this effect is very low compare to that of the gradient coating (FIG. 7). Besides, the cell selectivity is also very poor. The limited effect is mainly attributed to the low concentration of HA cell-resisting molecules on the most part of the gradient.

Comparing Example IV

The grafting of MA-HA and CREDV (SEQ ID NO: 1) peptide were carried out according to Example 1. The CREDV (SEQ ID NO: 1) peptide concentration gradient was fabricated according to Example 1.

Cell Adhesion Assay

The co-culture of ECs and fibroblasts was implemented by seeding $2.1 \times 10^4/cm^2$ of each type of cell in a 1:1 mixture of RPMI-1640 and DMEM. ECs and Smooth muscle cells were stained with 5 mg/mL DiO (green) and DiL (red), respectively, for 5 min before seeding.

Figure 22:
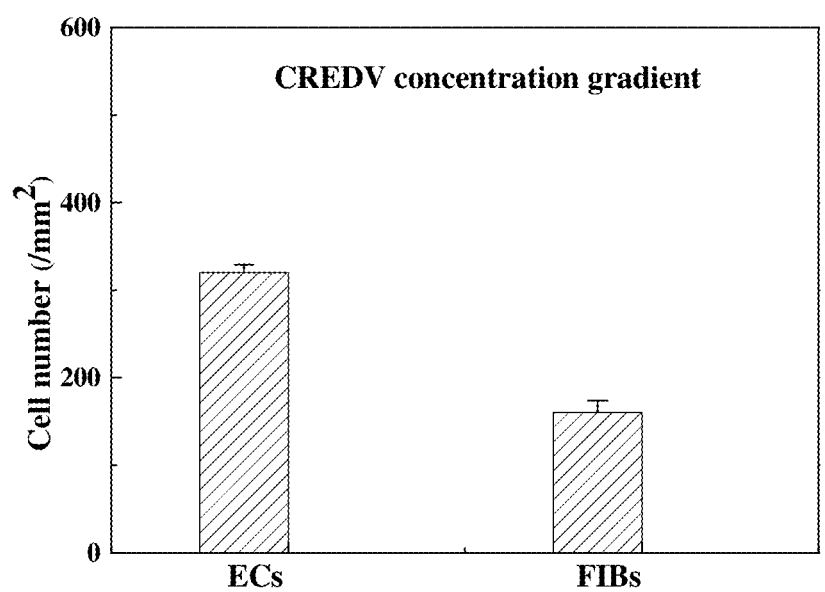
FIG. 22 is a graph showing numbers of ECs and fibroblasts cultured for 8 hours on CREDV (SEQ ID NO: 1) concentration gradient, in accordance with certain embodiments. The result indicated that more ECs adhered on the gradient coating compare to FIBs, proving again the selective adhesion of ECs.

As shown in FIG. 22, the number of ECs was approximately 2 folds of that of fibroblasts on the whole CREDV (SEQ ID NO: 1) density gradient, confirmed again the cell selective adhesion induced by the gradient coating.

Cell migration assay were carried out according to Example 1.

Figure 23:
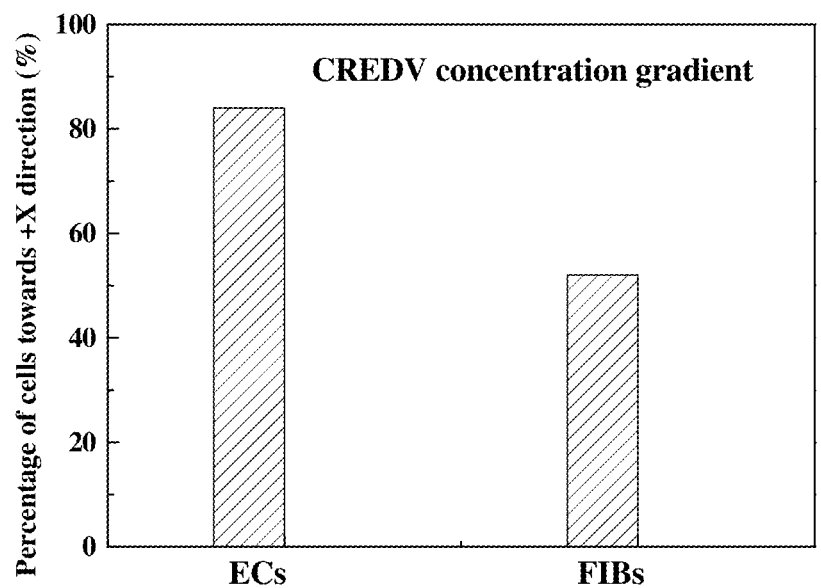
FIG. 23 is a graph showing percentage of ECs or fibroblasts migrating towards +X direction on concentration density gradient of CREDV (SEQ ID NO:1) in accordance with certain embodiments. The result proved again the selective directional migration of ECs was achieved by the gradient coating.

As shown in FIG. 23, 84% of the ECs moved toward the higher CREDV (SEQ ID NO: 1) peptide concentration of the gradient, which is much higher than fibroblasts. The result proved again the selective directional migration of ECs was achieved by the gradient coating.

Figure 11:
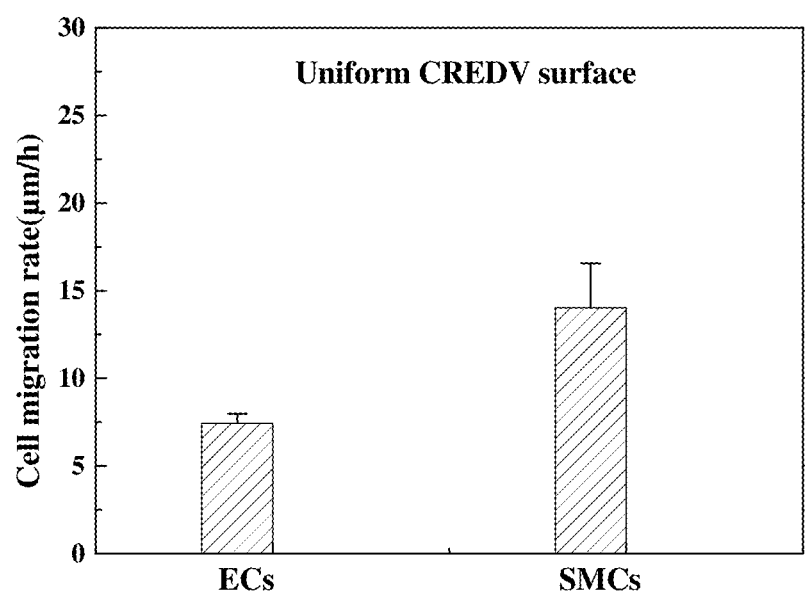
FIG. 11 is a graph showing migration rate of ECs and smooth muscle cells on uniform CREDV (SEQ ID NO: 1) peptide surface with MA-HA, in accordance with certain embodiments.
Figure 12:
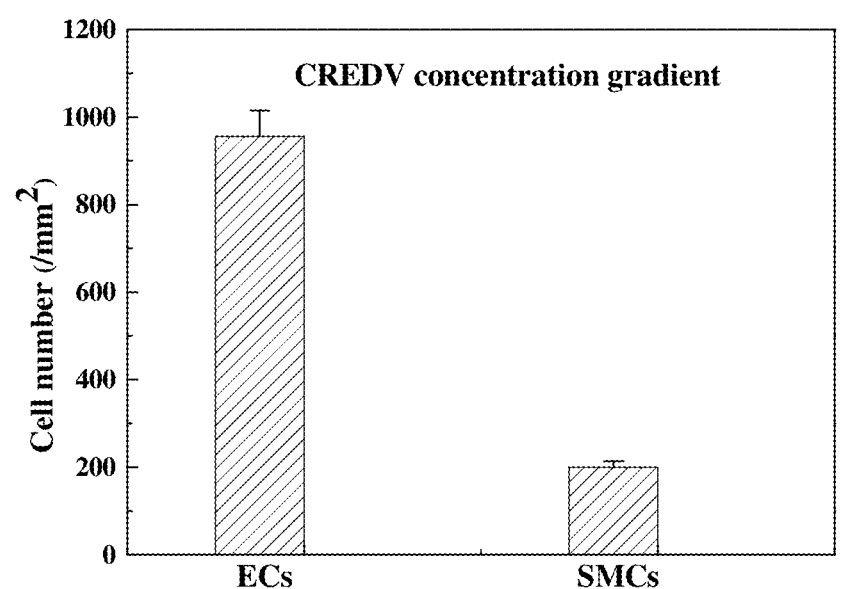
FIG. 12 is a graph showing numbers of ECs and smooth muscle cells cultured for 72 hours on CREDV (SEQ ID NO: 1) concentration gradient, in accordance with certain embodiments. Compared with FIG. 7, the results indicate a significant increase of ECs and nearly complete coverage of the surface (>80%) on the gradient coating as a result of combinational effect of selective adhesion and directional migration, while the number of SMCs was still very low.
Figure 13:
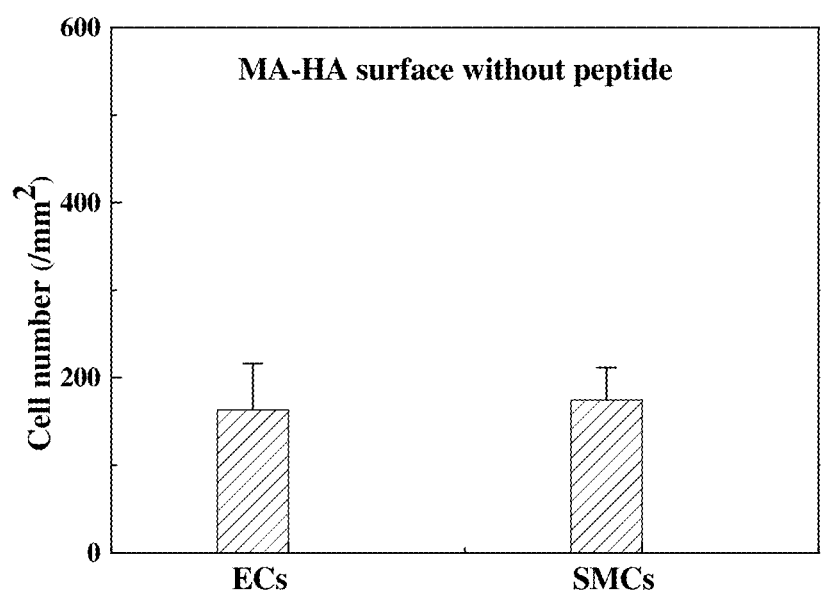
FIG. 13 is a graph showing numbers of ECs and smooth muscle cells cultured for 8 hours on MA-HA surface, in accordance with certain embodiments. The results suggested the universe cell-resisting effect to both ECs and SMCs of HA layer.
Figure 14:
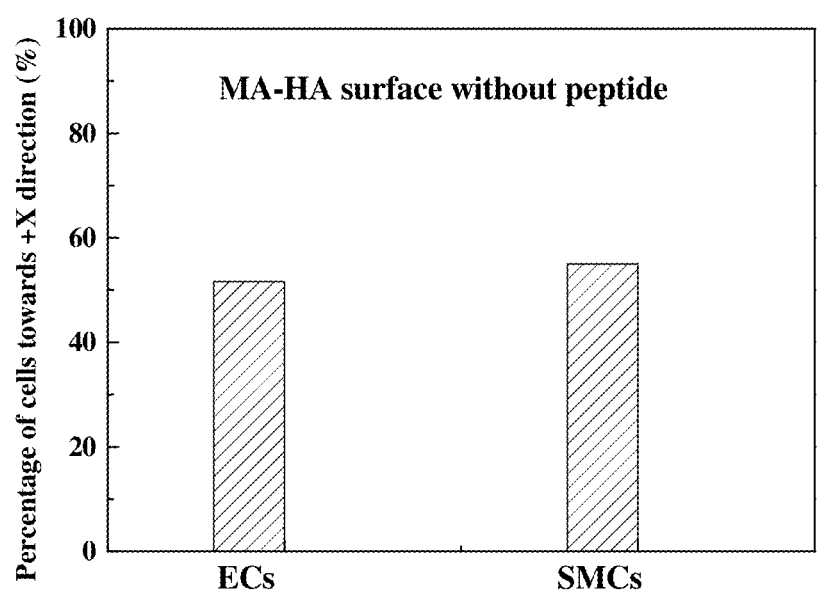
FIG. 14 is a graph showing percentage of ECs or smooth muscle cells migrating towards +X direction on MA-HA surface, in accordance with certain embodiments. The result indicated that the cell-resisting layer does not have ability to induce directional migration of both ECs and SMCs.
Figure 15:
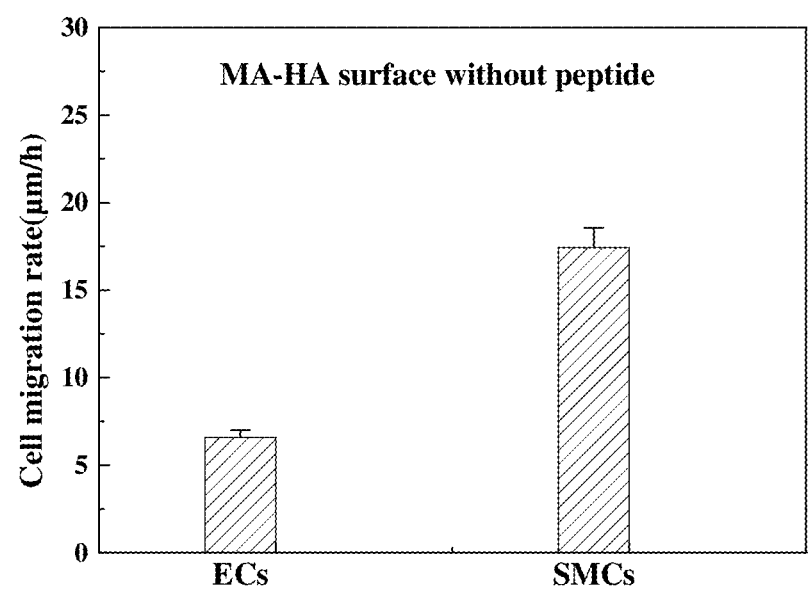
FIG. 15 is a graph showing migration rate of ECs and smooth muscle cells on MA-HA surface, in accordance with certain embodiments. The result indicated that SMCs move much faster than ECs on cell-resisting layer, which is similar to the pattern in natural environment.
Figure 16:
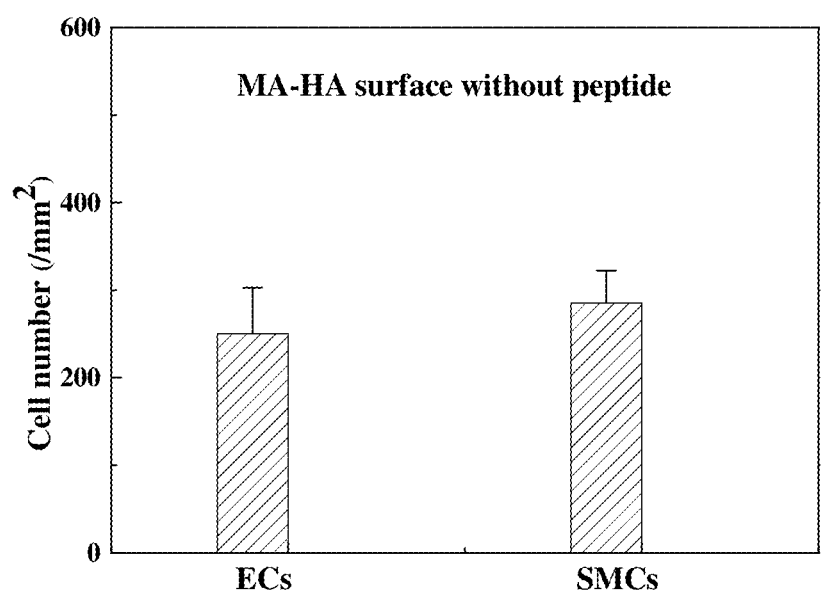
FIG. 16 is a graph showing numbers of ECs and smooth muscle cells cultured for 72 hours on MA-HA surface, in accordance with certain embodiments. Together with FIG. 13, the results suggested the long term cell-resisting effect to both ECs and SMCs of HA layer.
Figure 17:
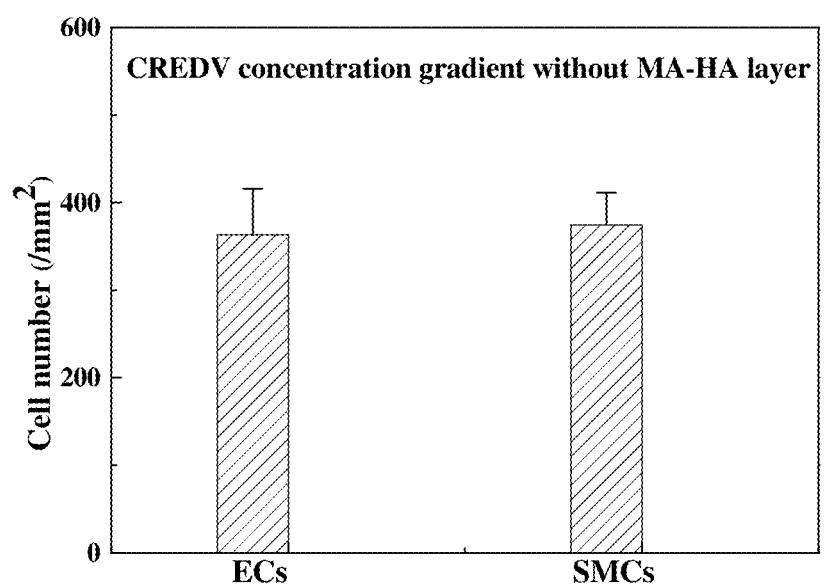
FIG. 17 is a graph showing numbers of ECs and smooth muscle cells cultured for 8 hours on CREDV (SEQ ID NO: 1) peptide concentration gradient without MA-HA, in accordance with certain embodiments. The result indicated that the peptide concentration gradient can support both ECs and SMCs adhesion without the HA cell-resisting layer.
Figure 18:
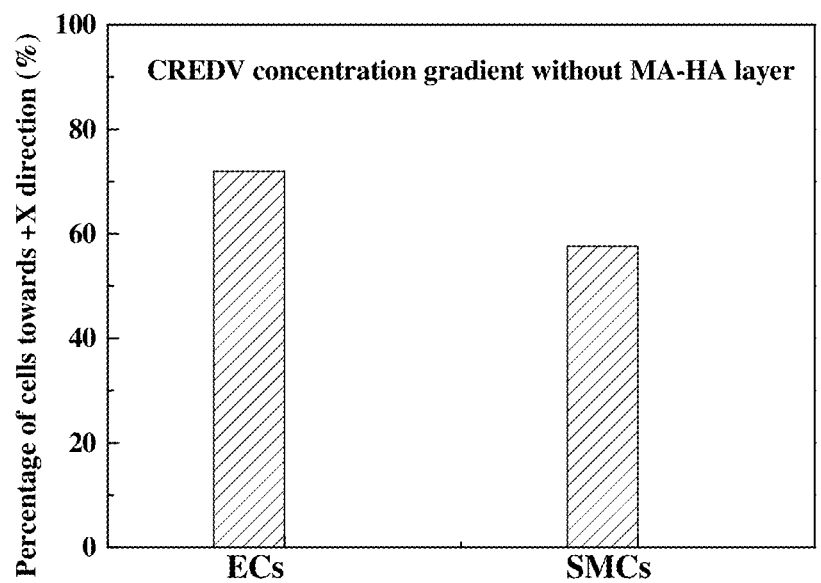
FIG. 18 is a graph showing percentage of ECs or smooth muscle cells migrating towards +X direction on CREDV (SEQ ID NO: 1) peptide density gradient without MA-HA surface, in accordance with certain embodiments. The result indicated that peptide concentration gradient alone can selectively induce directional migration of ECs to some extent, but the effect is smaller than gradient coating.
Figure 19:
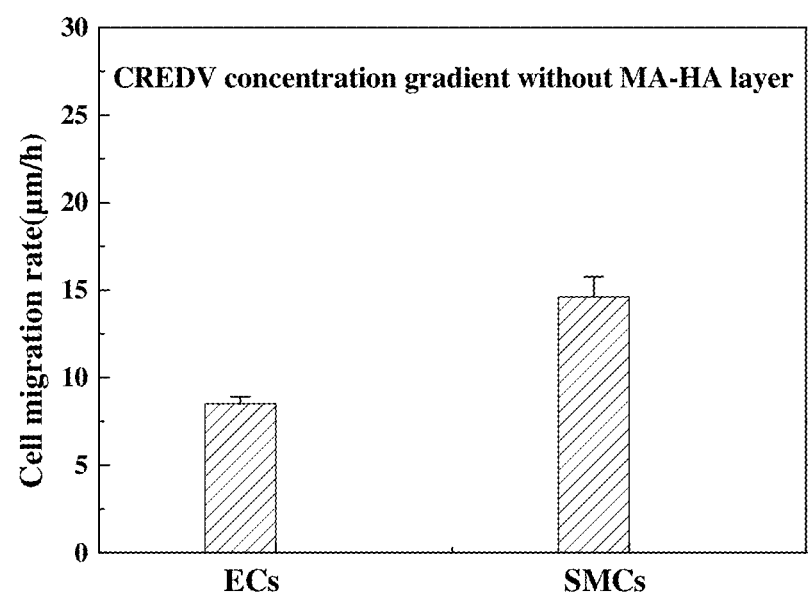
FIG. 19 is a graph showing migration rate of ECs and smooth muscle cells on CREDV (SEQ ID NO: 1) peptide concentration gradient without MA-HA, in accordance with certain embodiments. The result indicated that peptide concentration gradient alone cannot enhance the migration rate of ECs and SMCs.
Figure 20:
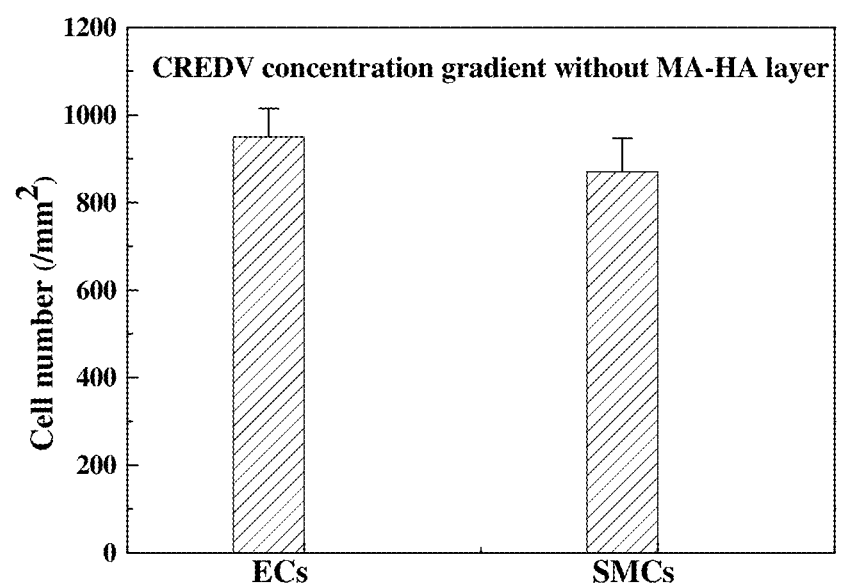
FIG. 20 is a graph showing numbers of ECs and smooth muscle cells cultured for 72 hours on CREDV (SEQ ID NO: 1) peptide concentration gradient without MA-HA, in accordance with certain embodiments. The result indicated that peptide concentration gradient alone can enhance the number of both ECs and SMCs, without cell selectivity.
Figure 21:
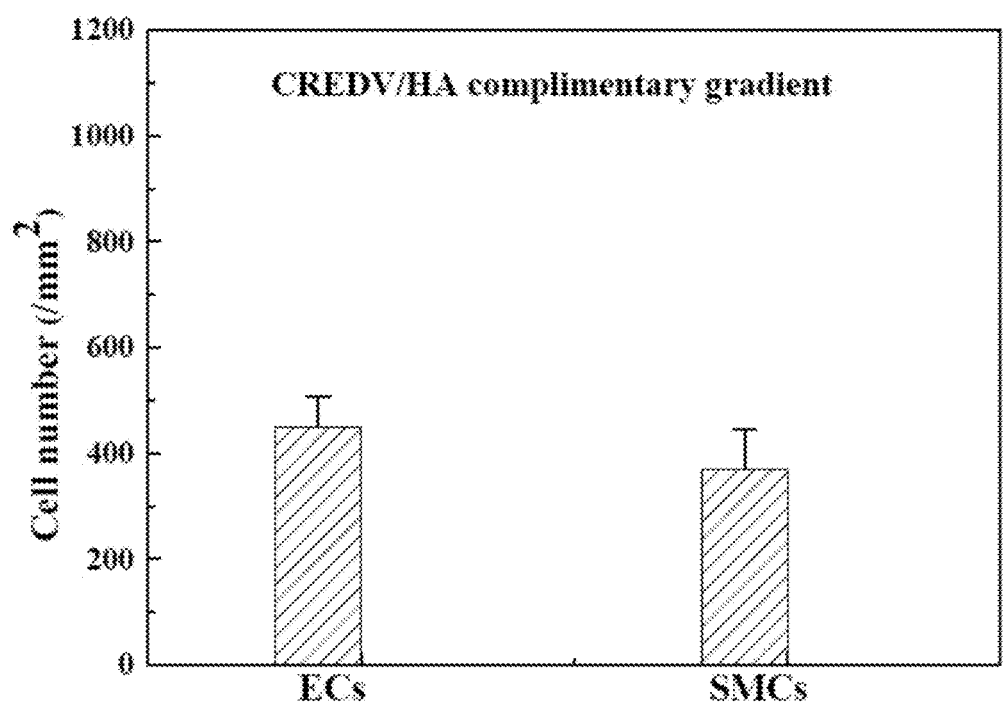
FIG. 21 is a graph showing numbers of ECs and smooth muscle cells cultured for 8 hours on CREDV (SEQ ID NO: 1)/HA complimentary gradient, in accordance with certain embodiments. The result indicated that the complimentary gradient can partially reject both ECs and SMCs adhesion to similar extent. But this effect is very low compare to that of the gradient coating (FIG. 7). The cell selectivity is also poor. The limited effect is mainly attributed to the low concentration of HA cell-resisting molecules on the most part of the gradient.
Figure 24:
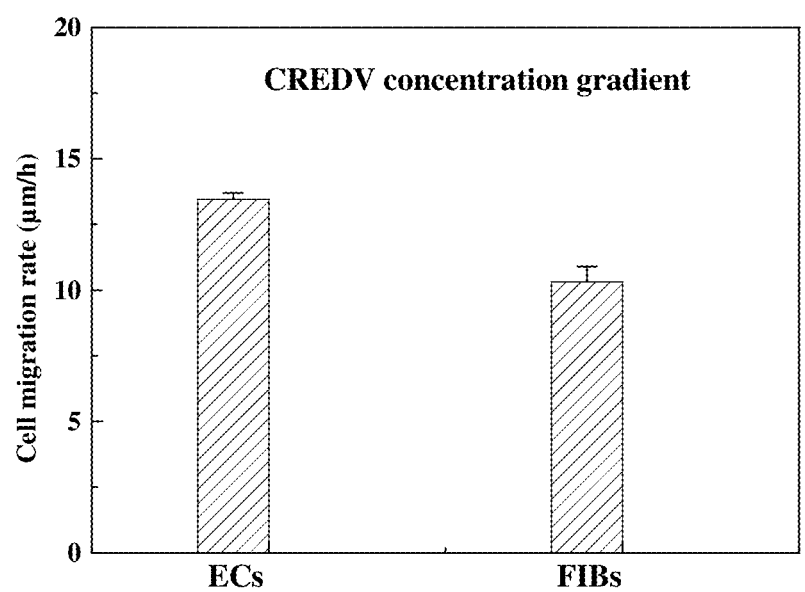
FIG. 24 is a graph showing migration rate of ECs and fibroblasts on CREDV (SEQ ID NO: 1) concentration gradient in accordance with certain embodiments. Compared to FIG. 11, the result clearly indicated that the migration rate of ECs was selectively enhanced by the gradient coating.

As shown in FIG. 24, endothelial cells migrated faster than smooth muscle cells on CREDV (SEQ ID NO: 1) peptide concentration gradient. Compared to FIG. 11, the result clearly indicated that the migration rate of ECs was selectively enhanced by the gradient coating.

Figure 25:
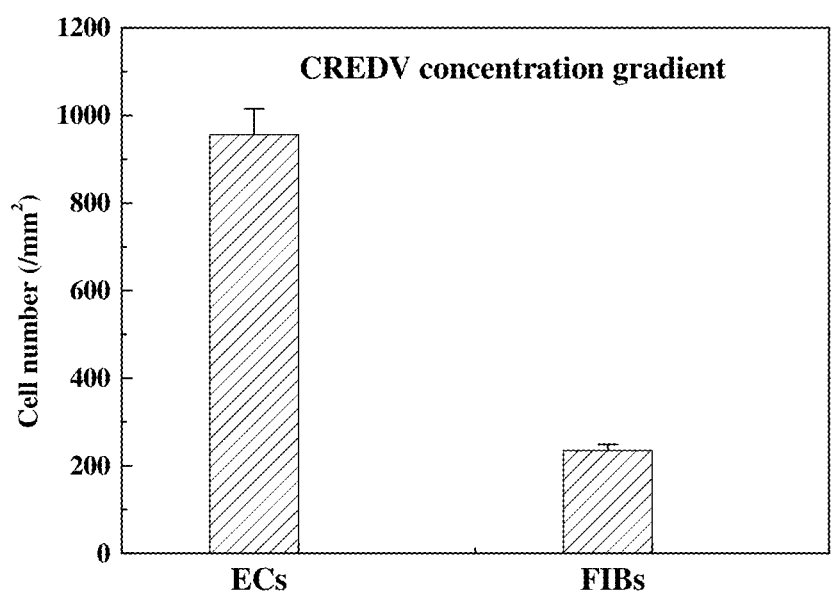
FIG. 25 is a graph showing numbers of ECs and fibroblasts cultured for 72 hours on CREDV (SEQ ID NO: 1) concentration gradient in accordance with certain embodiments.

As shown in FIG. 25, after being cultured for 72 h, number of ECs was almost 4-times to fibroblasts on CREDV (SEQ ID NO: 1) peptide concentration gradient.

Example 2

Grafting of Polyphosphoric Acid Choline

Polyphosphoric acid choline molecules were immobilized onto the surface of the PDA-coated PCL membrane via a condensation reaction between —COOH of polyphosphoric acid choline and —NH$_2$ of PDA under the presence of EDC/NHS. In brief, 200 mg polyphosphoric acid choline, 7 mg EDC and 12 mg NHS were dissolved in 100 mL water, and its pH value was adjusted to 5.5, in which the PDA-coated PCL membranes were incubated at 37° C. for 3 h, followed by washing with plenty of water.

Grafting of CGYL Peptides

To generate an CGYL (Cys-Gly-Tyr-Leu) (SEQ ID NO: 2) concentration gradient (total length was 10 mm), the CGYL (SEQ ID NO: 2) solution was slowly injected into a centrifuge tube by a micro-infusion pump at 37° C., where polyphosphoric acid choline-coated PCL membranes were placed vertically. The injection rate was adjustable with the longest reaction time of 60 min.

Cell adhesion and migration assays were carried out according to Example 1.

The number of ECs was approximately 2.3 fold of that of smooth muscle cells on the whole CGYL (SEQ ID NO: 2) concentration gradient.

86% of the ECs moved toward the higher CGYL (SEQ ID NO: 2) peptide concentration of the gradient, which is much higher than the smooth muscle cells (46%).

The migration rate of the smooth muscle cells slowed down slightly (10.4 µm/h). On CGYL (SEQ ID NO: 2) peptide concentration gradient, ECs (13.7 µm/h) migrated faster than the smooth muscle cells.

After being cultured for 72 h, number of ECs was almost 4.2-times higher than smooth muscle cells on CGYL (SEQ ID NO: 2) concentration gradient.

Example 3

Preparation of PDA-Coated Polyurethane (PU) Artificial Vascular Graft

PU tubes were prepared by dip-coating a 2% (w/v) PU/hexafluoroisopropanol solution mixed with 4% (w/v) NaCl onto the stainless steel cylinders with a diameter of 1.8 mm. The obtained PU tubes were immersed in a 2 mg/mL dopamine/tris-HCl (10 mM, pH=8.5) solution at 37° C. After a 12 h deposition, the PDA-coated PU tubes were removed and washed with water.

Grafting of MA-HA cell-resisting layer and CREDV (SEQ ID NO: 1) concentration gradient on PDA coated PU vessel were carried out according to Example 1.

Figure 26:
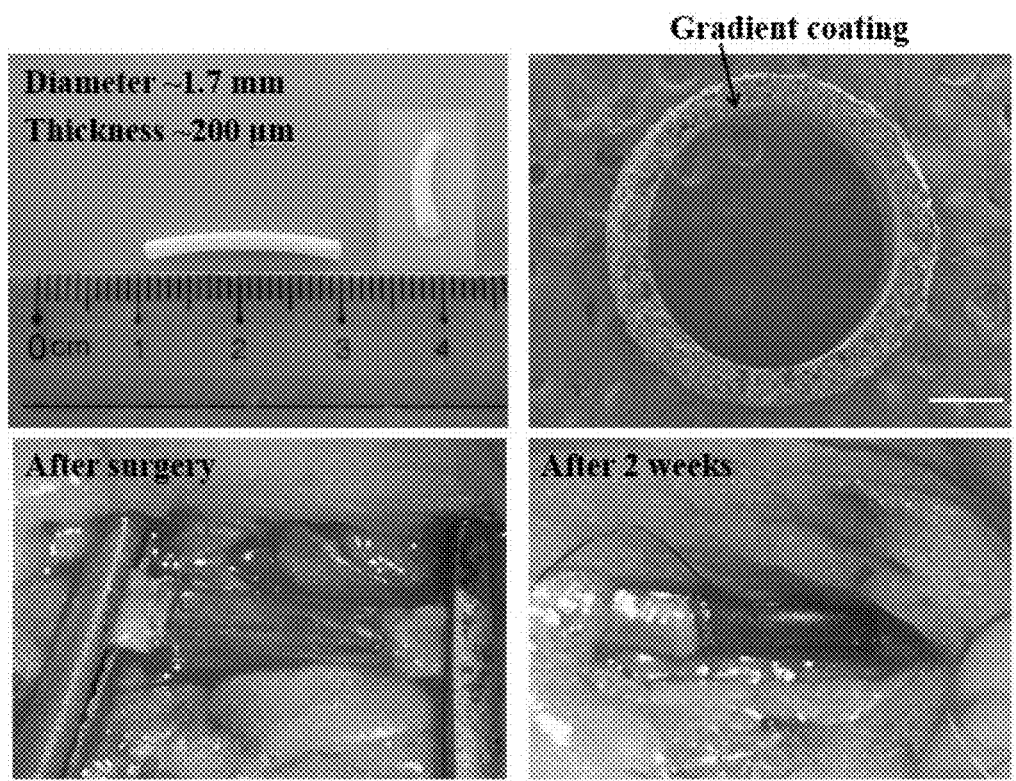
FIG. 26 is a graph showing characterization of polyurethane artificial vascular grafts and images of artificial vascular grafts sutured onto rat abdominal aorta.
Figure 27:
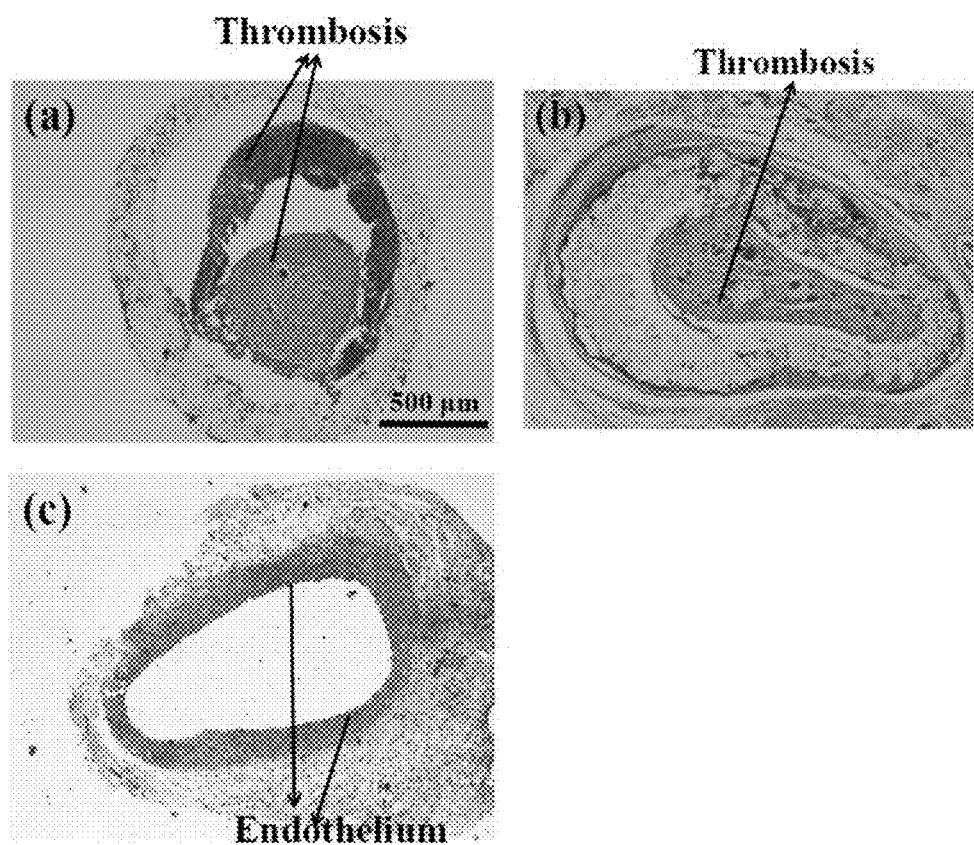
FIG. 27 is a graph showing H&E staining of artificial vascular grafts modified with (a) MA-HA, (b) CREDV (SEQ ID NO: 1) peptide concentration gradient without MA-HA layer, and (c) CREDV (SEQ ID NO: 1) peptide concentration gradient with MA-HA layer after being planted in vivo for 1 week, in accordance with certain embodiments. The result indicated that fully regeneration of endothelium is achieved on artificial vessel via concomitant MA-HA and CREDV (SEQ ID NO: 1) peptide gradient.

As shown in FIG. 26, rat abdominal aorta was cut into two parts, and the artificial vascular grafts were sutured onto the two ends of aorta. After 1 week, the artificial grafts were taken out and characterized with H&E staining As shown in FIG. 27, the artificial vascular grafts coating with CREDV (SEQ ID NO: 1) concentration gradient showed no thrombus compared to the ones coating with MA-HA. An intact endothelium was regenerated on the gradient coating. In contrast, an obvious thrombosis was observed in the vessels with only cell-resisting coating or with only peptide concentration gradient. No regeneration of endothelium was observed. The results showed the gradient material including MA-HA and CREDV (SEQ ID NO: 2) peptide concentration gradient can synergistically help the regeneration of endothelium, and may be used in artificial vascular grafts modification.

While the invention has been particularly shown and described as referenced to the embodiments thereof, those skilled in the art will understand that the foregoing and other changes in form and detail may be made therein without departing from the spirit and scope.

What is claimed is:

1. A gradient coating article configured to induce selective adhesion and directional migration of endothelial cells, comprising:
   a first layer of cell-resisting polymers that repels cell adhesion nondiscriminatory; and
   a second layer of peptides having specific affinity to, and operable to interact specifically with, endothelial cells, wherein the peptides are distributed in a concentration gradient configured to induce the endothelial cells to migrate towards the direction of increased peptide concentration at a rate that is higher than smooth muscle cells, and wherein the second layer is covalently linked to the first layer;
   wherein the first layer of cell-resisting polymers comprises evenly distributed polymer brushes of single polymer molecular thickness; and
   wherein the peptides are selected from the group consisting of Cys-Cys-Ala-Gly (SEQ ID NO: 3), Cys-Cys-Asn-Gly (SEQ ID NO: 4), Cys-Cys-Thr-Gly (SEQ ID NO: 5), Cys-Gly-Tyr-Leu (SEQ ID NO: 2), Cys-Ser-Val-Val-Tyr-Gly-Leu-Arg (SEQ ID NO: 6) and Cys-Arg-Glu-Asp-Val (SEQ ID NO: 1).

2. The gradient coating article according to claim 1, wherein the gradient coating is operable to repel at least 80% of non-endothelial cells and induce the adhesion of substantially all endothelial cells.

3. The gradient coating article according to claim 1, wherein the coating is operable to induce the directional migration of over 80% of endothelial cells, while exerting no impact on random migration of non-endothelial cells.

4. The gradient coating article according to claim 1, wherein the gradient coating is operable to induce the directional migration of the endothelial cells at a rate higher than when there is no gradient.

5. The gradient coating article according to claim 1, wherein the second layer of peptides is a single molecular layer.

6. The gradient coating article according to claim 1, wherein the first layer of cell-resisting polymers is linked to the second layer of peptides via conjugation by Michael addition reaction.

7. The gradient coating article according to claim 6, wherein the Michael addition reaction is between thiol group and carbon double bond.

8. The gradient coating article according to claim 1, wherein the cell-resisting polymers are selected from the following group: methacrylic anhydride modified hyaluronic acid with the molecular weight in the range of 500-200000 Da, and polyphosphoric acid choline with the molecular weight in the range of 500-200000 Da.

9. The gradient coating article according to claim 1, wherein the cell-resisting polymers have one end functionalized with a carboxyl group and have double bonds within repeating units.

10. The gradient coating article according to claim 1, wherein the thickness of the first layer of cell-resisting polymers is in the range of 0.5-5 nm.

11. The gradient coating article according to claim 1, wherein the thickness of the second layer of peptides is in the range of 0.5-5 nm.

12. The gradient coating article according to claim 1, further comprising:
   a substrate comprising biocompatible biodegradable polymers.

13. An implantable article configured to promote selective adhesion of endothelial cells and directional migration of the endothelial cells, comprising:
   a first layer of cell-resisting polymers that is uniform in composition and repels cell adhesion nondiscriminatory;
   a second layer of peptides having specific affinity to, and operable to interact specifically with, endothelial cells, wherein the peptides are distributed in a concentration gradient configured to induce the endothelial cells to migrate towards the direction of increased peptide concentration; and
   a substrate layer comprising biocompatible biodegradable polymers;
   wherein the peptides are selected from the group consisting of Cys-Cys-Ala-Gly (SEQ ID NO: 3), Cys-Cys-Asn-Gly (SEQ ID NO: 4), Cys-Cys-Thr-Gly (SEQ ID NO: 5), Cys-Gly-Tyr-Leu (SEQ ID NO: 2), Cys-Ser-Val-Val-Tyr-Gly-Leu-Arg (SEQ ID NO: 6) and Cys-Arg-Glu-Asp-Val (SEQ ID NO: 1).

14. The implantable article according to claim 13, wherein the endothelial cells migrate towards the direction of increased peptide concentration at a speed greater than that of smooth muscle cells.

15. The implantable article according to claim 13, wherein the first layer and the second layer are covalently linked.

16. The implantable article according to claim 13, wherein the implantable article is operable to form a part of an artificial blood vessel or stent to accelerate endothelium regeneration.

* * * * *

SEQUENCE LISTING

<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: synthesized

<400> SEQUENCE: 1

```
Cys Arg Glu Asp Val
1               5

<210> SEQ ID NO 2
<211> LENGTH: 4
<212> TYPE: PRT
<213> ORGANISM: Artificial Sequence
<220> FEATURE:
<223> OTHER INFORMATION: Synthesized

<400> SEQUENCE: 2

Cys Gly Tyr Leu
1

<210> SEQ ID NO 3
<211> LENGTH: 4
<212> TYPE: PRT
<213> ORGANISM: Artificial Sequence
<220> FEATURE:
<223> OTHER INFORMATION: Synthesized

<400> SEQUENCE: 3

Cys Cys Ala Gly
1

<210> SEQ ID NO 4
<211> LENGTH: 4
<212> TYPE: PRT
<213> ORGANISM: Artificial Sequence
<220> FEATURE:
<223> OTHER INFORMATION: Synthesized

<400> SEQUENCE: 4

Cys Cys Asn Gly
1

<210> SEQ ID NO 5
<211> LENGTH: 4
<212> TYPE: PRT
<213> ORGANISM: Artificial Sequence
<220> FEATURE:
<223> OTHER INFORMATION: Synthesized

<400> SEQUENCE: 5

Cys Cys Thr Gly
1

<210> SEQ ID NO 6
<211> LENGTH: 8
<212> TYPE: PRT
<213> ORGANISM: Artificial Sequence
<220> FEATURE:
<223> OTHER INFORMATION: Synthesized

<400> SEQUENCE: 6

Cys Ser Val Val Tyr Gly Leu Arg
1               5

<210> SEQ ID NO 7
<211> LENGTH: 4
<212> TYPE: PRT
<213> ORGANISM: Artificial Sequence
<220> FEATURE:
<223> OTHER INFORMATION: synthesized

<400> SEQUENCE: 7

Arg Glu Asp Val
```

```
1
<210> SEQ ID NO 8
<211> LENGTH: 5
<212> TYPE: PRT
<213> ORGANISM: Artificial Sequence
<220> FEATURE:
<223> OTHER INFORMATION: synthesized

<400> SEQUENCE: 8

Tyr Ile Gly Ser Arg
1               5
```